US00PP27803P2

(12) United States Plant Patent
Jensen

(10) Patent No.: US PP27,803 P2
(45) Date of Patent: Mar. 21, 2017

(54) ***ASTER* PLANT NAMED 'MYPOT0001'**

(50) Latin Name: *Aster novi-belgii*
Varietal Denomination: MYPOT0001

(71) Applicant: Bent Juhl Jensen, Malling (DK)

(72) Inventor: Bent Juhl Jensen, Malling (DK)

( * ) Notice: Subject to any disclaimer, the term of this patent is extended or adjusted under 35 U.S.C. 154(b) by 0 days.

(21) Appl. No.: 14/756,534

(22) Filed: Sep. 15, 2015

(51) Int. Cl.
*A01H 5/02* (2006.01)

(52) U.S. Cl.
USPC ..... Plt./355

(58) Field of Classification Search
USPC ..... Plt./355
CPC ..... A01H 5/025
See application file for complete search history.

*Primary Examiner* — Kent L Bell
(74) *Attorney, Agent, or Firm* — C. A. Whealy

(57) ABSTRACT

A new and distinct cultivar of *Aster* plant named 'MYPOT0001', characterized by its upright to outwardly spreading plant habit; moderately vigorous growth habit; freely branching growth habit; dense and bushy appearance; freely flowering habit; double type inflorescences with dark violet-colored ray florets; good postproduction longevity and good garden performance.

3 Drawing Sheets

Botanical designation: *Aster novi-belgii.*
Cultivar denomination: 'MYPOT0001'.

BACKGROUND OF THE INVENTION

The present invention relates to a new and distinct cultivar of *Aster* plant, botanically known as *Aster novi-belgii* and hereinafter referred to by the name 'MYPOT0001'.

The new *Aster* plant is a product of a planned breeding program conducted by the Inventor in Malling, Denmark. The objective of the breeding program is to create new vigorous *Aster* plants with freely branching habit and attractive double type inflorescences.

The new *Aster* originated from a cross-pollination in April, 2012 in Malling, Denmark of a proprietary selection of *Aster novi-belgii* identified as code number 09-131-002, not patented, as the female, or seed, parent with a proprietary selection of *Aster novi-belgii* identified as code number 07-099-003, not patented, as the male, or pollen, parent. The new *Aster* plant was discovered and selected by the Inventor as a single flowering plant within the progeny of the stated cross-pollination in a controlled greenhouse environment in Mailing, Denmark in August, 2013.

Asexual reproduction of the new *Aster* plant by terminal vegetative cuttings was first conducted in Malling, Denmark in September, 2013. Asexual reproduction by cuttings has shown that the unique features of this new *Aster* plant are stable and reproduced true to type in successive generations.

SUMMARY OF THE INVENTION

Plants of the new *Aster* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'MYPOT0001'. These characteristics in combination distinguish 'MYPOT0001' as a new and distinct *Aster* plant:

1. Upright to outwardly spreading plant habit.
2. Moderately vigorous growth habit.
3. Freely branching growth habit; dense and bushy appearance.
4. Freely flowering habit.
5. Double type inflorescences with dark violet-colored ray florets.
6. Good postproduction longevity and good garden performance.

Plants of the new *Aster* differ from plants of the female parent selection in the following characteristics:

1. Plants of the new *Aster* are larger than plants of the female parent selection.
2. Ray florets of plants of the new *Aster* are darker purple in color than ray florets of plants of the female parent selection.

Plants of the new *Aster* differ from plants of the male parent selection in the following characteristics:

1. Plants of the new *Aster* are bushier than and not as upright as plants of the male parent selection.
2. Leaf margins of plants of the new *Aster* are slightly serrate whereas leaf margins of plants of the male parent selection are entire.
3. Inflorescences of plants of the new *Aster* produce a scarce amount of pollen whereas inflorescences of plants of the male parent selection produce pollen.

Plants of the new *Aster* can be compared to plants of *Aster novi-belgii* 'Victoria Fanny', disclosed in U.S. Plant Pat. No. 13,360. In side-by-side comparisons conducted in Malling, Denmark, plants of the new *Aster* differed from plants of 'Victoria Fanny' in the following characteristics:

1. Leaves of plants of the new *Aster* were narrower than leaves of plants of 'Victoria Fanny'.
2. Ray florets of plants of the new *Aster* were darker violet in color than ray florets of plants of 'Victoria Fanny'.

BRIEF DESCRIPTION OF THE PHOTOGRAPHS

The accompanying photographs illustrate the overall appearance of the new *Aster* plant showing the colors as true as it is reasonably possible to obtain in colored reproductions of this type. Colors in the photographs may differ slightly from the color values cited in the detailed botanical description which accurately describe the colors of the new *Aster* plant.

The photograph on the first sheet is a side perspective view of a typical flowering plant of 'MYPOT0001' grown in a container.

The photograph on the second sheet is a close-up view of the upper surface of a typical leaf of 'MYPOT0001'.

The photograph on the third sheet is a close-up view of a typical flowering plant of 'MYPOT0001'.

DETAILED BOTANICAL DESCRIPTION

The aforementioned photographs and following observations and measurements describe plants grown during the winter and early spring in 10.5-cm containers in a glass-covered greenhouse in Malling, Denmark and under cultural practices which approximate those generally used in commercial *Aster* production. During the production of the plants, day and night temperatures averaged 20° C. Plants were pinched two times and were twelve weeks old when the photographs and description were taken. In the following description, color references are made to The Royal Horticultural Society Colour Chart, 2007 Edition, except where general terms of ordinary dictionary significance are used.

Botanical classification: *Aster novi-belgii* 'MYPOT0001'.

Parentage:

*Female, or seed, parent*.—Proprietary selection of *Aster novi-belgii* identified as code number 09-131-002, not patented.

*Male, or pollen, parent*.—Proprietary selection of *Aster novi-belgii* identified as code number 07-099-003, not patented.

Propagation:

*Type*.—Terminal vegetative cuttings.

*Time to initiate roots, summer and winter*.—About eight days at temperatures about 20° C.

*Time to produce a rooted young plant, summer and winter*.—About 20 days at temperatures about 20° C.

*Root description*.—Medium in thickness, fibrous; typically white in color, actual color of the roots is dependent on substrate composition, water quality, fertilizers, substrate temperature and physiological age of roots.

*Rooting habit*.—Moderately freely branching; dense.

Plant description:

*Plant and growth habit*.—Herbaceous double type potted *Aster* plant; upright to outwardly spreading plant habit; broad inverted triangle; strong and freely branching habit with about 18 lateral branches developing per plant, pinching enhances branching potential; moderately vigorous growth habit.

*Plant height*.—About 19.1 cm.

*Plant width*.—About 27.9 cm.

*Lateral branches*.—Length: About 11.8 cm. Diameter: About 3 mm. Internode length: About 1.1 cm. Aspect: About 15° to 40° from vertical. Strength: Strong. Texture: Pubescent. Luster: Moderately glossy. Color: Close to 137B.

Leaf description:

*Arrangement*.—Alternate, simple; sessile.

*Length*.—About 6.2 cm.

*Width*.—About 1.4 cm.

*Shape*.—Lanceolate to narrowly oblanceolate.

*Apex*.—Acute.

*Base*.—Truncate.

*Margin*.—Irregularly and shallowly serrate.

*Texture, upper surface*.—Slightly rugose, glabrous.

*Texture, lower surface*.—Very slightly rugose, glabrous.

*Luster, upper surface*.—Slightly glossy.

*Luster, lower surface*.—Very slightly glossy.

*Color*.—Developing leaves, upper surface: Close to 137C. Developing leaves, lower surface: Close to 138C. Fully expanded leaves, upper surface: Close to between N137A and 147A; venation, close to 146A. Fully expanded leaves, lower surface: Close to 137B; venation, 147B.

Inflorescence description:

*Type and arrangement*.—Double type inflorescence form with oblanceolate-shaped ray florets; inflorescences borne on terminal and axillary branches above and beyond the foliar plane; ray and disc florets arranged acropetally on a capitulum.

*Fragrance*.—None detected.

*Flowering response*.—Under natural conditions, plants flower during the autumn in Denmark; plants begin flowering about four to six weeks after planting.

*Inflorescence longevity*.—Inflorescences maintain good substance for about two to three weeks on the plant; inflorescences persistent.

*Quantity of inflorescences*.—Freely flowering habit with about twelve inflorescences per lateral branch and about 216 inflorescences developing per plant.

*Inflorescence buds*.—Height: About 1 cm. Diameter: About 8 mm. Shape: Broadly elliptic. Color: Close to 137C; towards the apex, close to 85A.

*Inflorescence size*.—Diameter: About 3.3 cm. Depth (height): About 1.7 cm. Diameter of disc: About 4 mm, inconspicuous.

*Receptacles*.—Height: About 3 mm. Diameter: About 2 mm. Shape: Rhomboidal. Color: Close to 143C.

*Ray florets*.—Length: About 1.5 cm. Width: About 2.5 mm. Shape: Oblanceolate. Apex: Obtuse. Base: Cuneate. Margin: Entire. Texture, upper and lower surfaces: Smooth, glabrous. Luster, upper surface: Matte, velvety. Luster, lower surface: Slightly glossy. Orientation: Initially upright, then about 70° from vertical to perpendicular to peduncle. Number of ray florets per inflorescence: About 260 arranged in numerous whorls. Color: When opening, upper surface: Close to N87B. When opening, lower surface: Close to N88C to N88D. Fully opened, upper surface: Close to N87A and N87B; color does not change with development. Fully opened, lower surface: Close to N88C to N88D; color does not change with development.

*Disc florets*.—Quantity and arrangement: If present, about two to four per inflorescence and randomly arranged at the center of the receptacle; disc florets inconspicuous. Length: About 6 mm. Diameter: About 3 mm. Shape: Tubular, elongated; five free apices are acute. Texture, inner and outer surfaces: Smooth, glabrous. Luster, inner and outer surfaces: Moderately glossy. Color, immature, inner and outer surfaces: Apex: Close to 150D. Mid-section and base: Close to 145C and 145D. Color, mature, inner and outer surfaces: Apex: Close to 84C and 84D. Mid-section and base: Close to 150D.

*Phyllaries*.—Quantity and arrangement: About 45 per inflorescence arranged in about three whorls. Length: About 6 mm. Width: About 1 mm. Shape: Lanceolate. Apex: Acute. Base: Cuneate. Margin: Entire. Texture, upper and lower surfaces: Smooth, glabrous. Luster, upper and lower surfaces: Slightly glossy. Color, upper surface: Close to 138B. Color, lower surface: Close to 137C to 137D.

*Peduncles*.—Length, terminal peduncle: About 2 mm. Length, fourth peduncle: About 8 mm. Length, seventh peduncle: About 1.1 cm. Diameter: About 1 mm. Angle: Terminal inflorescences, on top of lateral branch; axillary inflorescences, about 50° from lateral branch. Strength: Moderately strong, flexible. Texture: Pubescent. Color: Close to 137B.

*Reproductive organs*.—Androecium: Present on disc florets only. Quantity of stamens per floret: Five. Filament length: About 5 mm. Filament color: Close to 150D. Anther shape: Lanceolate. Anther length: About 1 mm. Anther color: Close to 164A. Pollen amount: Scarce. Pollen color: Close to 13A to 13B. Gynoecium: Present on ray and disc florets. Quantity of pistils per floret: One. Pistil length: About 7 mm. Stigma shape: Cleft, two to three-parted, decurrent. Stigma color: Close to 159D. Style length: About 5 mm. Style color: Close to 155A. Ovary color: Close to 145C to 145D.

*Seeds and fruits*.—Seed and fruit production have not been observed on plants of the new *Aster*.

Disease & pest resistance: Plants of the new *Aster* have not been observed to be resistant to pathogens and pests common to *Aster* plants.

Garden performance: Plants of the new *Aster* have been observed to be tolerant to rain, wind and high temperatures of about 35° C., and to be hardy to USDA Hardiness Zone 4.

It is claimed:

1. A new and distinct *Aster* plant named 'MYPOT0001' as illustrated and described.

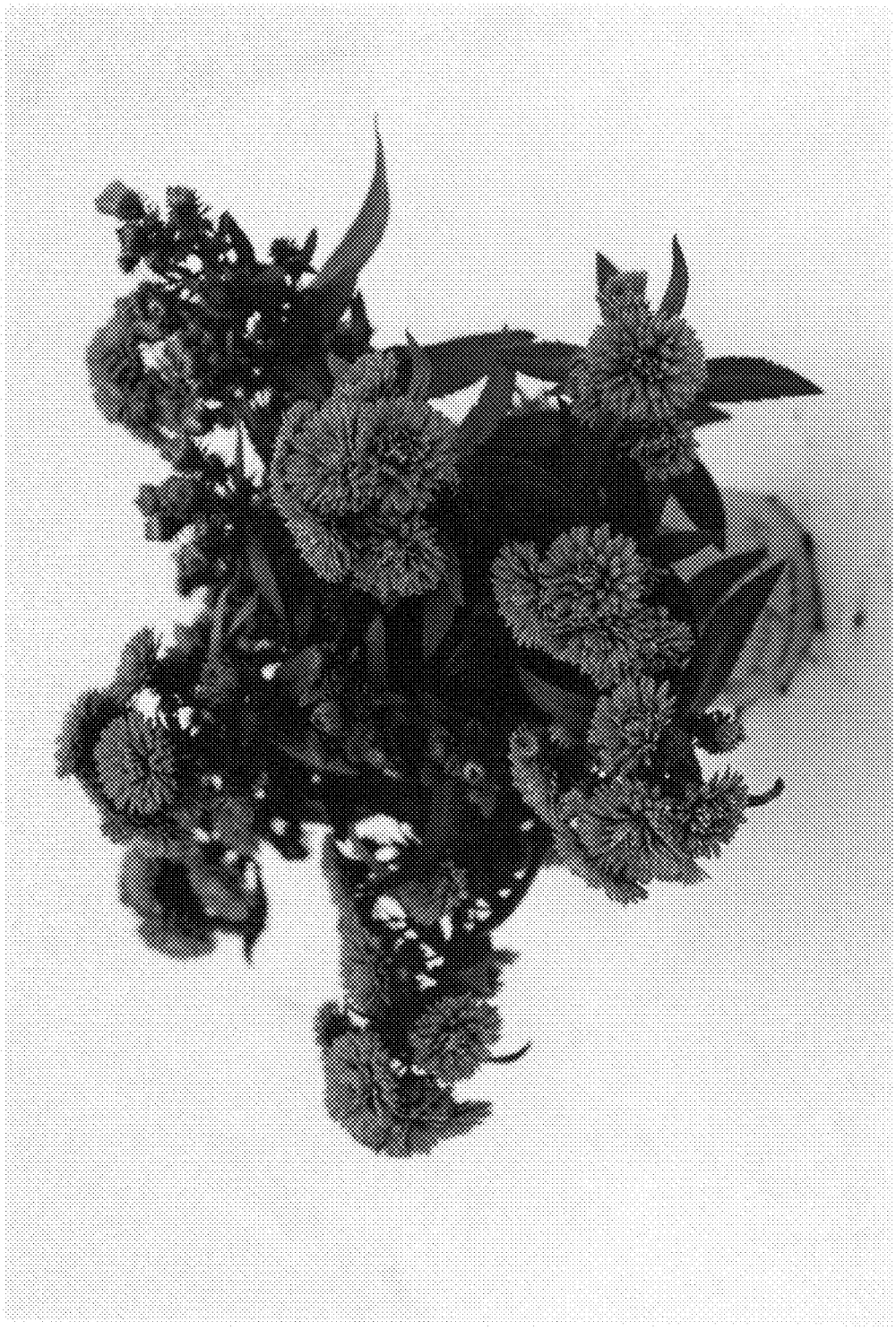

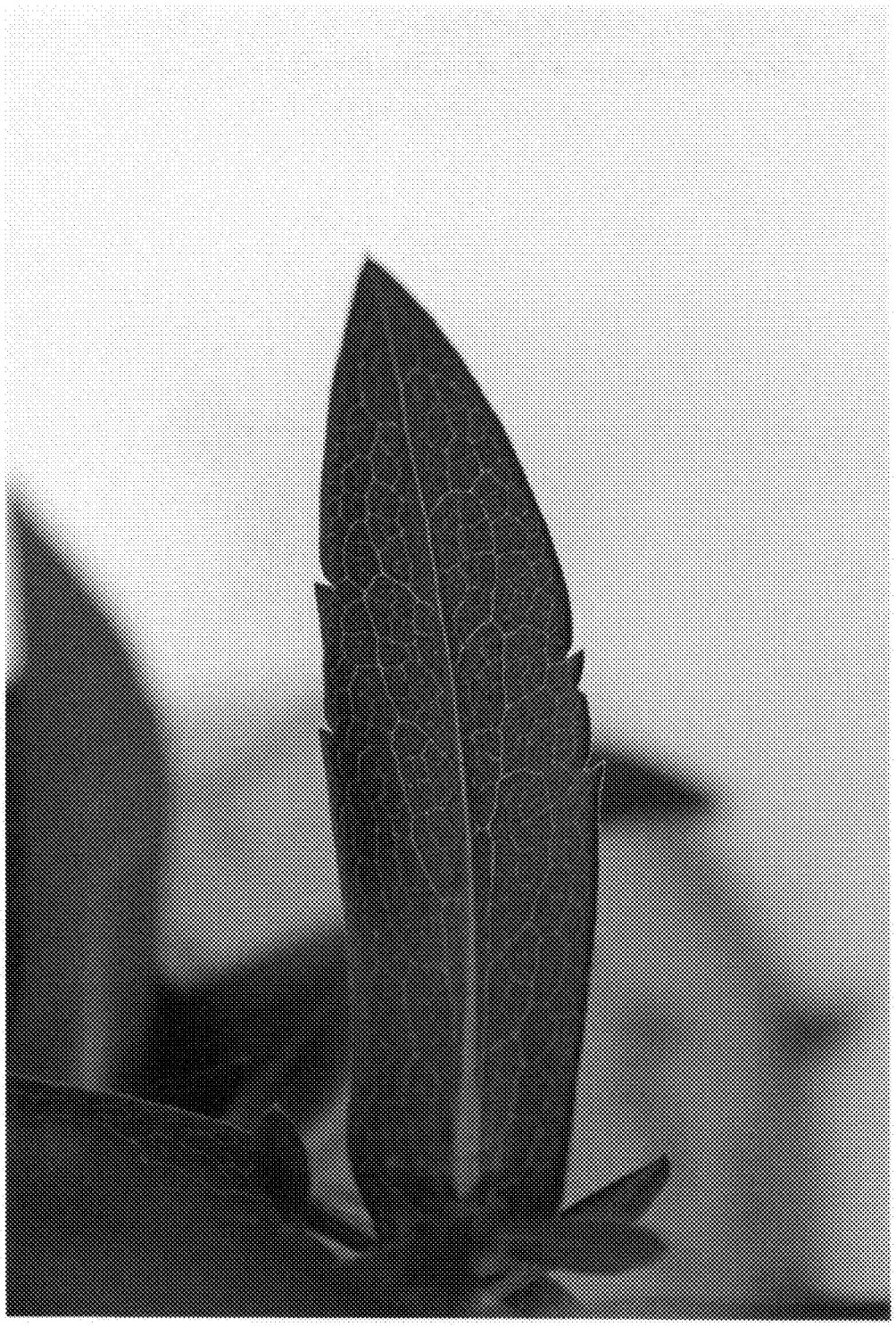

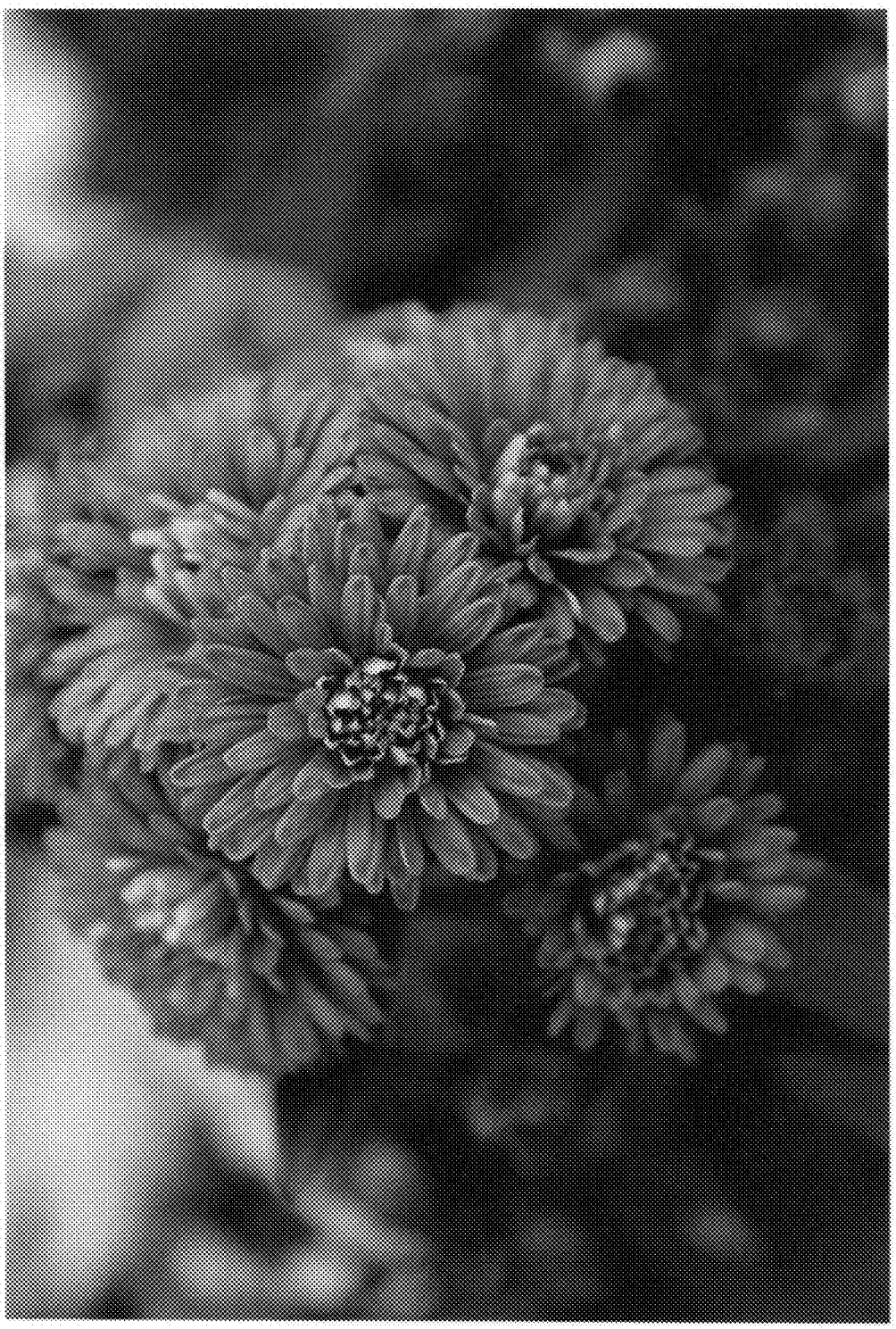

* * * * *